(12) United States Patent
Pallikaris et al.

(10) Patent No.: US 7,708,750 B2
(45) Date of Patent: May 4, 2010

(54) DEVICE FOR SEPARATING THE EPITHELIUM LAYER FROM THE SURFACE OF THE CORNEA OF AN EYE

(75) Inventors: Ioannis Pallikaris, Gazi of Heraklion (GR); Harilaos S. Ginis, Heraklion (GR)

(73) Assignee: FOS Holdings S.A., Luxembourg (LU)

( * ) Notice: Subject to any disclaimer, the term of this patent is extended or adjusted under 35 U.S.C. 154(b) by 1544 days.

(21) Appl. No.: 10/786,350

(22) Filed: Feb. 25, 2004

(65) Prior Publication Data

US 2004/0167555 A1    Aug. 26, 2004

Related U.S. Application Data

(63) Continuation of application No. 09/911,356, filed on Jul. 23, 2001, now Pat. No. 7,156,859.

(51) Int. Cl.
*A61F 9/00* (2006.01)
(52) U.S. Cl. .................................. 606/166; 604/294
(58) Field of Classification Search .............. 606/5, 606/6, 107, 161, 166, 205, 167; 604/294
See application file for complete search history.

(56) References Cited

U.S. PATENT DOCUMENTS

| | | | |
|---|---|---|---|
| 2,881,500 A | 4/1959 | Furness | |
| 4,198,132 A | 4/1980 | Seger et al. | |
| 4,346,482 A | 8/1982 | Tennant et al. | |
| 4,381,007 A | 4/1983 | Doss | |
| 4,414,974 A | 11/1983 | Dotson et al. | |
| 4,417,579 A | 11/1983 | Soloviev et al. | |
| 4,451,254 A * | 5/1984 | Dinius et al. | 604/62 |
| 4,473,076 A | 9/1984 | Williams et al. | |
| 4,501,274 A | 2/1985 | Skjaerpe | |
| 4,576,164 A | 3/1986 | Richeson | |
| 4,646,720 A | 3/1987 | Peyman et al. | |
| 4,659,584 A | 4/1987 | Schlik | |
| 4,662,370 A | 5/1987 | Hoffmann et al. | |
| 4,662,881 A | 5/1987 | Nordan | |

(Continued)

FOREIGN PATENT DOCUMENTS

CA    2355478 A1    2/2002

(Continued)

OTHER PUBLICATIONS

International Search Report from corresponding international application No. PCT/US05/28188, Sep. 13, 2007.

(Continued)

*Primary Examiner*—Michael J Milano
*Assistant Examiner*—Victor X Nguyen
(74) *Attorney, Agent, or Firm*—Brinks Hofer Gilson & Lione

(57) ABSTRACT

An automated mechanical device separates the epithelial layer of a cornea from the cornea. The device includes a separator such as a plate, wire or dull blade. The device can preserve a separated epithelial layer as a disk without rupturing the disk and without substantial epithelial cell loss. The epithelial layer is separated from the cornea without cutting the cornea.

18 Claims, 9 Drawing Sheets

U.S. PATENT DOCUMENTS

| | | | |
|---|---|---|---|
| 4,665,914 A | 5/1987 | Tanne | |
| 4,676,790 A | 6/1987 | Kern | |
| 4,688,570 A | 8/1987 | Kramer et al. | |
| 4,715,858 A | 12/1987 | Lindstrom | |
| 4,731,079 A | 3/1988 | Stoy | |
| 4,770,172 A | 9/1988 | L'Esperance, Jr. | |
| 4,773,414 A | 9/1988 | L'Esperance, Jr. | |
| 4,775,361 A | 10/1988 | Jacques et al. | |
| 4,793,344 A | 12/1988 | Cumming et al. | |
| 4,798,204 A | 1/1989 | L'Esperance, Jr. | |
| 4,838,266 A | 6/1989 | Koziol et al. | |
| 4,840,175 A | 6/1989 | Peyman | |
| 4,844,060 A | 7/1989 | Krumeich | |
| 4,858,324 A | 8/1989 | Wiech, Jr. | |
| 4,865,033 A | 9/1989 | Krumeich et al. | |
| 4,884,570 A | 12/1989 | Krumeich et al. | |
| 4,941,093 A | 7/1990 | Marshall et al. | |
| 4,955,894 A | 9/1990 | Herman | |
| 5,011,498 A | 4/1991 | Krumeich et al. | |
| 5,063,942 A | 11/1991 | Kilmer et al. | |
| 5,098,444 A | 3/1992 | Feaster | |
| 5,108,388 A | 4/1992 | Trokel | |
| 5,108,412 A | 4/1992 | Krumeich et al. | |
| 5,133,726 A * | 7/1992 | Ruiz et al. | 606/166 |
| 5,133,747 A | 7/1992 | Feaster | |
| 5,163,934 A | 11/1992 | Munnerlyn | |
| 5,163,956 A | 11/1992 | Liu et al. | |
| 5,171,318 A | 12/1992 | Gibson et al. | |
| 5,192,316 A | 3/1993 | Ting | |
| 5,196,027 A | 3/1993 | Thompson et al. | |
| 5,213,720 A | 5/1993 | Civerchia | |
| 5,215,104 A | 6/1993 | Stenert | |
| 5,269,795 A | 12/1993 | Arnott | |
| 5,279,611 A | 1/1994 | McDonnell et al. | |
| 5,292,329 A | 3/1994 | Werner | |
| 5,308,355 A * | 5/1994 | Dybbs | 606/166 |
| 5,312,330 A | 5/1994 | Klopotek | |
| 5,312,413 A | 5/1994 | Eaton et al. | |
| 5,318,044 A | 6/1994 | Kilmer et al. | |
| 5,318,047 A | 6/1994 | Davenport et al. | |
| 5,319,424 A | 6/1994 | Tomiyama | |
| 5,323,788 A | 6/1994 | Silvestrini et al. | |
| 5,368,604 A | 11/1994 | Kilmer et al. | |
| 5,374,515 A | 12/1994 | Parenteau et al. | |
| 5,376,099 A | 12/1994 | Ellis et al. | |
| 5,395,385 A | 3/1995 | Kilmer et al. | |
| 5,403,335 A * | 4/1995 | Loomas et al. | 606/161 |
| 5,423,801 A | 6/1995 | Marshall et al. | |
| 5,423,843 A | 6/1995 | Werner | |
| 5,437,658 A | 8/1995 | Muller et al. | |
| 5,458,610 A | 10/1995 | Feaster | |
| 5,462,739 A | 10/1995 | Dan et al. | |
| 5,464,417 A | 11/1995 | Eick | |
| 5,490,849 A | 2/1996 | Smith | |
| 5,492,135 A | 2/1996 | DeVore et al. | |
| 5,496,339 A | 3/1996 | Koepnick | |
| 5,505,723 A | 4/1996 | Muller | |
| 5,522,888 A | 6/1996 | Civerchia | |
| 5,549,597 A | 8/1996 | Shimmick et al. | |
| 5,549,599 A | 8/1996 | Sumiya | |
| 5,549,632 A | 8/1996 | Lai | |
| 5,554,155 A | 9/1996 | Awh et al. | |
| 5,556,406 A | 9/1996 | Gordon et al. | |
| 5,569,292 A | 10/1996 | Schemberger et al. | |
| 5,571,124 A | 11/1996 | Zelman | |
| 5,599,341 A | 2/1997 | Mathis et al. | |
| 5,603,709 A | 2/1997 | Johnson | |
| 5,613,965 A | 3/1997 | Muller | |
| 5,616,139 A | 4/1997 | Okamoto | |
| 5,630,810 A | 5/1997 | Machat | |
| 5,632,757 A | 5/1997 | Arnott | |
| 5,634,920 A | 6/1997 | Hohla | |
| 5,647,865 A | 7/1997 | Swinger | |
| 5,649,943 A | 7/1997 | Amoils | |
| 5,658,303 A | 8/1997 | Koepnick | |
| 5,676,679 A | 10/1997 | Simon et al. | |
| 5,685,998 A | 11/1997 | Shannon et al. | |
| 5,690,657 A | 11/1997 | Koepnick | |
| 5,699,810 A | 12/1997 | Pallikaris | |
| 5,700,274 A | 12/1997 | Feaster | |
| 5,711,762 A | 1/1998 | Trokel | |
| 5,716,633 A | 2/1998 | Civerchia | |
| 5,722,427 A | 3/1998 | Wakil et al. | |
| 5,722,971 A | 3/1998 | Peyman | |
| 5,735,843 A | 4/1998 | Trokel | |
| 5,740,803 A | 4/1998 | Gray et al. | |
| 5,741,245 A | 4/1998 | Cozean et al. | |
| 5,766,200 A | 6/1998 | Mazurek et al. | |
| 5,779,696 A | 7/1998 | Berry et al. | |
| 5,779,711 A | 7/1998 | Kritzinger et al. | |
| 5,779,724 A | 7/1998 | Werner | |
| 5,782,852 A | 7/1998 | Foggia et al. | |
| 5,795,351 A | 8/1998 | Clapham | |
| 5,803,923 A | 9/1998 | Singh-Derewa et al. | |
| 5,807,380 A | 9/1998 | Dishler | |
| 5,807,381 A | 9/1998 | Lieberman | |
| 5,827,641 A | 10/1998 | Parenteau et al. | |
| 5,833,701 A | 11/1998 | Gordon | |
| RE35,974 E | 12/1998 | Davenport et al. | |
| 5,851,213 A | 12/1998 | Berleth et al. | |
| 5,857,995 A | 1/1999 | Thomas et al. | |
| RE36,150 E | 3/1999 | Gupta | |
| 5,879,363 A * | 3/1999 | Urich | 606/167 |
| 5,904,678 A | 5/1999 | Pop | |
| 5,919,185 A | 7/1999 | Peyman | |
| 5,934,285 A | 8/1999 | Kritzinger et al. | |
| 5,941,874 A | 8/1999 | Hohla | |
| 5,947,987 A | 9/1999 | Gordon et al. | |
| 5,964,748 A | 10/1999 | Peyman | |
| 5,970,984 A | 10/1999 | Wakil et al. | |
| 5,975,351 A | 11/1999 | DeLacerda | |
| 5,980,543 A | 11/1999 | Carriazo et al. | |
| 5,984,916 A | 11/1999 | Lai | |
| 5,989,272 A | 11/1999 | Barron et al. | |
| 5,997,559 A | 12/1999 | Ziemer | |
| 6,006,756 A | 12/1999 | Shadduck | |
| 6,030,376 A | 2/2000 | Arashima et al. | |
| 6,030,398 A | 2/2000 | Klopotek | |
| 6,036,683 A | 3/2000 | Jean et al. | |
| 6,045,562 A | 4/2000 | Amano et al. | |
| 6,050,999 A * | 4/2000 | Paraschac et al. | 606/107 |
| 6,059,775 A | 5/2000 | Nielson | |
| 6,068,625 A | 5/2000 | Clapman | |
| 6,068,640 A | 5/2000 | Gordon et al. | |
| 6,071,293 A | 6/2000 | Krumeich | |
| 6,079,417 A | 6/2000 | Fugo | |
| 6,083,236 A | 7/2000 | Feingold | |
| 6,099,541 A | 8/2000 | Klopotek | |
| 6,110,202 A | 8/2000 | Barraquer et al. | |
| 6,126,668 A | 10/2000 | Bair et al. | |
| 6,129,723 A | 10/2000 | Anderson et al. | |
| 6,132,421 A | 10/2000 | Clapham | |
| 6,162,210 A | 12/2000 | Shadduck | |
| 6,171,336 B1 | 1/2001 | Sawusch | |
| 6,187,053 B1 | 2/2001 | Minuth | |
| 6,203,538 B1 | 3/2001 | Peyman | |
| 6,203,555 B1 | 3/2001 | Amano | |
| 6,206,900 B1 | 3/2001 | Tabatabaei et al. | |
| 6,217,571 B1 | 4/2001 | Peyman | |
| 6,221,067 B1 | 4/2001 | Peyman | |
| 6,228,025 B1 | 5/2001 | Hipps et al. | |
| 6,231,583 B1 | 5/2001 | Lee | |
| 6,241,721 B1 | 6/2001 | Cozean et al. | |
| 6,254,619 B1 | 7/2001 | Garabet et al. | |

| | | | |
|---|---|---|---|
| 6,264,648 B1 | 7/2001 | Peyman | |
| 6,280,435 B1 | 8/2001 | Odrich et al. | |
| 6,280,469 B1 | 8/2001 | Terry et al. | |
| 6,280,470 B1 | 8/2001 | Peyman | |
| 6,293,938 B1 | 9/2001 | Muller et al. | |
| 6,302,896 B1 | 10/2001 | Carriazo et al. | |
| 6,306,075 B1 | 10/2001 | Shadduck | |
| 6,322,216 B1 | 11/2001 | Yee et al. | |
| 6,331,177 B1 | 12/2001 | Munnerlyn et al. | |
| 6,335,006 B1 | 1/2002 | Miller | |
| 6,350,236 B1 | 2/2002 | Hipps et al. | |
| 6,379,370 B1 | 4/2002 | Feinsod | |
| 6,391,055 B1 | 5/2002 | Ikada et al. | |
| 6,409,345 B1 | 6/2002 | Molebny et al. | |
| 6,436,093 B1 | 8/2002 | Ruiz et al. | |
| 6,451,039 B1 | 9/2002 | Richey, Jr. et al. | |
| 6,458,141 B1 | 10/2002 | Peyman | |
| 6,464,692 B1 | 10/2002 | Ruiz et al. | |
| 6,468,206 B1 | 10/2002 | Hipps et al. | |
| 6,468,642 B1 | 10/2002 | Bray et al. | |
| 6,482,153 B1 | 11/2002 | Hipps et al. | |
| 6,497,701 B2 | 12/2002 | Shimmick et al. | |
| 6,506,198 B1 | 1/2003 | Amano | |
| 6,530,916 B1 | 3/2003 | Shimmick | |
| 6,543,453 B1 | 4/2003 | Klima et al. | |
| 6,544,286 B1 | 4/2003 | Perez | |
| 6,551,307 B2 | 4/2003 | Peyman | |
| 6,589,558 B1 | 7/2003 | Pallikaris | |
| 6,599,305 B1 | 7/2003 | Feingold | |
| 6,607,527 B1 | 8/2003 | Ruiz et al. | |
| 6,623,497 B1 | 9/2003 | Feingold | |
| 6,626,924 B1 | 9/2003 | Klopotek | |
| 6,638,271 B2 | 10/2003 | Munnerlyn et al. | |
| 6,666,855 B2 | 12/2003 | Somani et al. | |
| 6,673,062 B2 | 1/2004 | Yee et al. | |
| 6,702,807 B2 | 3/2004 | Peyman | |
| 6,702,832 B2 | 3/2004 | Ross et al. | |
| 6,706,036 B2 | 3/2004 | Lai | |
| 6,730,073 B2 | 5/2004 | Bruce | |
| 2001/0027314 A1 | 10/2001 | Peyman | |
| 2001/0053917 A1 | 12/2001 | Lin et al. | |
| 2002/0026101 A1 | 2/2002 | Bookwalter | |
| 2002/0026240 A1 | 2/2002 | Pallikaris et al. | |
| 2002/0052596 A1 | 5/2002 | Pallikaris et al. | |
| 2002/0052614 A1 | 5/2002 | GeBauer | |
| 2002/0077640 A1 | 6/2002 | Metzger | |
| 2002/0107508 A1 | 8/2002 | Burnett | |
| 2002/0116056 A1 | 8/2002 | Kirk | |
| 2002/0119141 A1 | 8/2002 | Karageozian | |
| 2002/0135736 A1 | 9/2002 | Stark et al. | |
| 2002/0138069 A1 | 9/2002 | Peyman | |
| 2003/0011745 A1 | 1/2003 | Molebny et al. | |
| 2003/0018347 A1 | 1/2003 | Pallikaris et al. | |
| 2003/0018348 A1 | 1/2003 | Pallikaris et al. | |
| 2003/0083743 A1 | 5/2003 | Perez | |
| 2003/0105521 A1 | 6/2003 | Perez | |
| 2003/0139755 A1 | 7/2003 | Dybbs | |
| 2003/0220653 A1 | 11/2003 | Perez | |
| 2004/0059361 A1 | 3/2004 | Feingold | |
| 2004/0073246 A1 | 4/2004 | Aufure et al. | |
| 2004/0097955 A1 | 5/2004 | Feingold | |
| 2004/0167555 A1 | 8/2004 | Pallikaris et al. | |
| 2004/0220599 A1 | 11/2004 | Pallikaris et al. | |

FOREIGN PATENT DOCUMENTS

| | | |
|---|---|---|
| CN | 1259032 | 7/2000 |
| DE | 27 50 492 A1 | 5/1979 |
| DE | 38 38 253 A1 | 5/1990 |
| DE | 3838253 A1 | 5/1990 |
| DE | G93 15 396.1 U1 | 2/1994 |
| DE | 297 14 266 U1 | 12/1997 |
| DE | 297 12 339 U1 | 1/1998 |
| DE | 298 05 538 U1 | 7/1998 |
| DE | 298 10 603 U1 | 12/1998 |
| DE | 198 47 089 A1 | 5/2000 |
| DE | 201 07 259 U1 | 12/2001 |
| DE | 201 15 585 U1 | 2/2002 |
| DE | 100 51 215 A1 | 5/2002 |
| DE | 101 19 477 A1 | 10/2002 |
| DE | 200 23 239 U1 | 8/2003 |
| DE | 202 04 635 U1 | 9/2003 |
| DE | 102 14 917 A1 | 10/2003 |
| DE | 102 32 169 A1 | 2/2004 |
| EP | 0 659 955 A1 | 8/1994 |
| EP | 0 659 955 B1 | 1/1997 |
| EP | 0 873 735 A1 | 10/1998 |
| EP | 0 956 840 A2 | 11/1999 |
| EP | 0956 840 A2 | 11/1999 |
| EP | 1 114 628 A1 | 7/2001 |
| EP | 1 181 913 A2 | 2/2002 |
| EP | 1 199 055 A1 | 4/2002 |
| EP | 1 350 492 A2 | 10/2003 |
| FR | 2 691 625 A3 | 12/1993 |
| JP | 2000 245766 | 9/2000 |
| JP | 2002119532 A | 4/2002 |
| WO | WO 94/17851 | 8/1994 |
| WO | WO 97/20529 | 6/1997 |
| WO | WO 98/53774 | 12/1998 |
| WO | WO 01/93791 A1 | 12/2001 |
| WO | WO 01/97729 A1 | 12/2001 |
| WO | WO 02/06883 A2 | 1/2002 |
| WO | WO 03/007989 A1 | 2/2003 |
| WO | WO 03/026542 A1 | 4/2003 |
| WO | WO 03/061518 A2 | 7/2003 |
| WO | WO 2006/017835 | 2/2006 |

OTHER PUBLICATIONS

Chinese Office Action from corresponding Chinese Patent Application No. CN 200580032387.8, dated Aug. 21, 2009.

Terry J. Van Der Werff, D.Phil., *A New Single-Parameter Ocular Rigidity Function*, vol. 92, pp. 391-395 (1981).

Winston Roberts, M.D., and J. William Rogers, M.D., *Postural Effects on Pressure and Ocular Rigidity Measurements*, pp. 111-118 (Assumed published prior to filing date).

Peter P. Purslow, PhD, Wojciech S.S. Karwatowski, FROCOphth, *Ocular Elasticity*, pp. 1686-1692 (1996).

Joseph N. Simone, MD and Marc M. Whitacre, MD, *The Effect of Intraocular Gas and Fluid Volumes on Intraocular Pressure*, Ophthalmology, vol. 97, No. 2, pp. 238-243 (1990).

John E. Eisenlohr, M.E. Langham and A.E. Maumenee, *Manometric Studies of the Pressure-Volume Relationship in Living and Enucleated Eyes of Individual Human Subjects*, Brit. J. Ophthal., vol. 46, pp. 536-548 (1962).

Richard F. Brubaker, *Tonometry*, Clinical Ophthalmology, vol. 3, Chap. 47, pp. 1-7 (Assumed to be published before filing date).

Jonas S. Friedenwald, M.D., *Tonometer Calibration*, pp. 108-123 (1957).

Carsten Edmund, *Corneal Elasticity and Ocular Rigidity in Normal and Keratoconic Eyes*, Acta Ophthalmologica, vol. 66, pp. 134-140 (1988).

Ephraim Friedman, MD, Sara Krupsky, MD, Anne Marie Lane, MPH, Setsuko S. Oak, Eric S. Friedman, MD, Kathleen Egan, MPH, Evangelos S. Gragoudas, MD, *Ocular Blood Flow Velocity in Age-Related Macular Degeneration*, Ophthalmology, vol. 102, No. 4, pp. 640-646 (1995).

Mark W. Johnson, MD, Dennis P. Han, MD, Kenneth E. Hoffman, MS, *The Effect of Scleral Buckling on Ocular Rigidity*, Ophthalmology, vol. 97, pp. 190-195 (1990).

Evangelos S. Gragoudas, MD, Suresh R. Chandra, MD, Ephraim Friedman, MD, Michael L. Klein, MD, Micael Van Buskirk, MD, *Disciform Degeneration of the Macula*, Arch Ophthalmol, vol. 94, pp. 755-757 (1976).

Ephraim Freidman, MD, *A Hemodynamic Model of the Pathogenesis of Age Related Macular Degeneration*, pp. 1-14 (1997).

Jeffrey B. Robin, MD *Overview of Microkeratomes,* (Assumed to be published before filing date).

Ioannis G. Pallikaris, MD, Maria E. Papatzanaki, MD, Evdoxia Z. Stathi, MD, Oliver Frenschock, and Anthimos Georgiadis, PhD, *Laser in Situ Keratomileusis,* Lasers in Surgery and Medicine, vol. 10 pp. 463-468, 1990.

Stephen L. Trokel, M.D., R. Srinivasan, PhD., and Bodil Baren, B.A., *Excimer Laser Surgery of the Cornea,* vol. 96, No. 6, pp. 710-715, 1983.

David S. Gartry, FRCS, FCOphth, Malcolm G. Kerr Muir, FRCS, FCOphth, John Marshall, PhD., *Photorefractive Keratectomy with an Argon Fluoride Excimer Laser: A Clinical Study,* vol. 7, pp. 420-435, Nov./Dec. 1991.

Stephen L. Trokel, M.D., R. Srinivasan, PhD., and Bodil Baron, B.A., *Excimer Laser Surgery of the Cornea,* vol. 96, No. 6, pp. 710-715, 1983.

David S. Gartry, FRCS, FCOphth, Malcolm G. Kerr Muir, FRCS, FCOphth, John Marshall, PhD., *Photorefractive Keratectomy with an Argon Fluoride Excimer Laser: A Clinical Study,* vol. 7, pp. 420-435, Nov./Dec. 1991.

Ioannis G. Pellikaris, MD, Maria E. Papatzanakl, MD, Evdoxia Z. Stathi, MD, Oliver Frenschock, and Anthimos Georgiadis, PhD, "*Laser in Situ Keratomileusis,* Lasers in Surgery and Medicine," vol. 10, 1990. pp. 483-468.

Chen, K.H. et al. "*Transplantation of Adult Human Corneal Endothelium Ex Vivo: A Morphologic Study,*" Cornea, vol. 20, No. 7, 2001, pp. 731-737.

Joo, C-K et al. "*Repopulation of Denuded Murine Descemet's Membrane with Life-Extended Murine Corneal Endothelial Cells as a Model for Corneal Cell Transplantation,*" Graefes Archive for Clinical and Experimental Ophthalmology; vol. 238, No. 2, 2000, pp. 174-180.

Schwab, I. R. and Isseroff, R. R., "Bioenginered Corneas—The Promise and the Challenge," The New England Journal of Medicine; vol. 343, No. 2, 2000, pp. 136-138.

Teal, R. J-F. et al. "*Reconstruction of Damaged Corneas by Transplantation of Autologous Limbal Epithelial Cells*" The New England Journal of Medicine; vol. 343, No. 2, Jul. 13, 2000, pp. 86-93.

Chen, C. C. et al. "*Human Corneal Epithelial Cell Viability and Morphology after Dilute Alcohol Exposure*" Investigative Ophtomalogy & Visual Science; vol. 43, No. 8. Aug. 2002. pp. 2593-2602.

Pallikarls, Ioannis G., M.D., et al. "*Epi-LASIK: Comparative Histological Evaluation of Mechanical and Alcohol-Assisted Epithelial Separation,*" J Cataract Refract Surg; vol. 29, Aug. 2003, pp. 1496-1501.

EPI-Peeler Drawing by Geuder, Germany, produced from Chris Lohmann presentation. Apr. 2004, One page.

Lohmann, Chris P., MD, PhD, "Epi-Lasik Epi-Tome", presented Apr. 2004, Seville, Spain, 47 pages.

Photo using a light microscope of a blade manufactured by GeBauer, evaluated in Athens, Greece, on or about Jun. 2004. One page.

Soloway, Barrie D., "US Clinical Studies with the Epik for E-Lasik" performed by Moria (Epi-Lasik and Lamellar Surgery), presented Sep. 18, 2004, Parts, France, Twenty-three pages.

Gebauer announcements of clinical results for the first 100 Epi-LASIK patients treated in Europe, Mar. 5, 2004, One page.

\* cited by examiner

DEVICE FOR SEPARATING THE EPITHELIUM LAYER FROM THE SURFACE OF THE CORNEA OF AN EYE

RELATED APPLICATION

This application is a Continuation of U.S. patent application Ser. No. 09/911,356, filed Jul. 23, 2001, now U.S. Pat. No. 7,156,859 entitled "Device for Separating the Epithelium Layer From the Surface of the Cornea of an Eye" which is hereby incorporated by reference herein.

BACKGROUND

LASIK (Laser-Assisted In Situ Keratomileusis) is a surgical procedure intended to reduce a person's dependency on glasses or contact lenses. LASIK permanently changes the shape of the cornea, the clear covering of the front of the eye, using an excimer laser. A device, called a microkeratome, is used to cut a flap in the cornea. A hinge is left at one end of this flap. The flap is folded back revealing the stroma, the middle-section of the cornea. Pulses from a computer-controlled laser vaporize a portion of the stroma and the flap is replaced. It is important that the knife used during the LASIK procedure is sharp, otherwise the quality of the procedure and the healing time are poor. Additionally the knife has to be sharp in order to produce consistent and reproducible flaps. There are some complications related to the use of microkeratomes. The most common complication is the creation of an irregular flap, for example, a half flap, buttonhole, or total cup. These complications represent irregular incisions of the cornea, a situation that can permanently degrade visual performance.

Before LASIK, PRK (Photo-Refractive Keratectomy) was used to correct the curvature of the cornea. A physician could scrape away a superficial layer, e.g., the epithelium, of the cornea. After the superficial layer was removed, laser treatment was applied on to the exposed surface of the cornea. A problem existed, however, in that the healing period for the eye typically lasted for a week, much longer than the healing period of LASIK. Also, the patient experienced a lot of pain during healing. Typically in PRK a disposable contact lens is used to cover the treated area of the cornea and help reduce postoperative pain.

In another technique, LASEK (Laser Epithelial Keratomileusis) the epithelial layer is separated from the surface of the cornea in a manner that the separated epithelial layer can be preserved. First, the epithelium is treated with and alcohol solution to partially devitalize it. Once the exact surface area of treatment is determined, a few drops of a weak alcohol solution is applied to the surface of the cornea and allowed to stay in contact with the epithelium for a few seconds. This weak alcohol solution is then rinsed off the surface of the eye. The function of the weak alcohol solution is to loosen the epithelial layer (50 microns) and to allow it to be peeled back in a sheet of epithelial cells, thereby exposing the underlying cornea. This is not to be confused with LASIK, which actually uses a microkeratome instrument to create a flap of both epithelium and the front part of the stromal tissue measuring anywhere between 130 to 180 microns.

In LASEK, the epithelium-only layer is laid back in a similar fashion to LASIK, but consists of only epithelium, not corneal stroma. Once the epithelial cells have been laid out of the way, the laser is applied to the surface of the cornea in the exact same fashion as in PRK. Once the laser treatment has been completed, the epithelial layer is laid back into place and a soft contact lens is placed over the eye as in PRK. The epithelial cells, which were partly devitalized by the weak alcohol solution, are laid over the treatment area and may serve as a facilitator of new epithelium healing underneath. The alcohol-devitalized epithelium falls off the eye, similar to a scab, in 5-10 days. These devitalized epithelial cells do not become the new surface of the eye, but simply serve as a protective agent in addition to the contact lens to facilitate comfort and healing of the new underlying epithelium. Alcohol treatment of the epithelium results in a severe amount of epithelial cell loss, a fact that may render the epithelial disk not usable, due to the reduced durability and adhesion on to the cornea.

Thus, there is a need for an automated corneal epithelium separator that addresses the above problems by separating the epithelial layer as a whole in a mechanical way, not chemical.

BRIEF SUMMARY

To help correct an imperfect vision of a patient's eye, an automated mechanical device separates the epithelial layer from the cornea of a patient's eye from the cornea. After the epithelial layer is separated from the cornea, a laser is used to help correct imperfections in the cornea. Thereafter, the epithelial layer is placed back on the cornea to reduce the visual rehabilitation period and reduce postoperative pain.

In one aspect, the device includes a separator such as a plate, wire or dull blade. The device can preserve a separated epithelial layer as a disk without rupturing the disk and without substantial epithelial cell loss. The epithelial layer is separated from the cornea without cutting the cornea.

DETAILED DESCRIPTION

To help correct an imperfect vision of a patient's eye, an automated mechanical device separates the epithelial layer from the cornea of a patient's eye from the cornea. A separator, such as a plate, wire or dull blade is used to separate the epithelial layer of the cornea from the basal membrane. In this way, the automated mechanical device can preserve the separated epithelial layer as a disk without rupturing the disk and without substantial epithelial cell loss, less than 5-10% loss, to ensure viability and stability of the epithelial disk after replacement on the surface of the cornea. After the epithelial layer is separated from the cornea, a laser is used to help correct imperfections in the cornea. Thereafter, the epithelial layer is placed back on the cornea to aid in the healing process of the eye.

Figure 1:
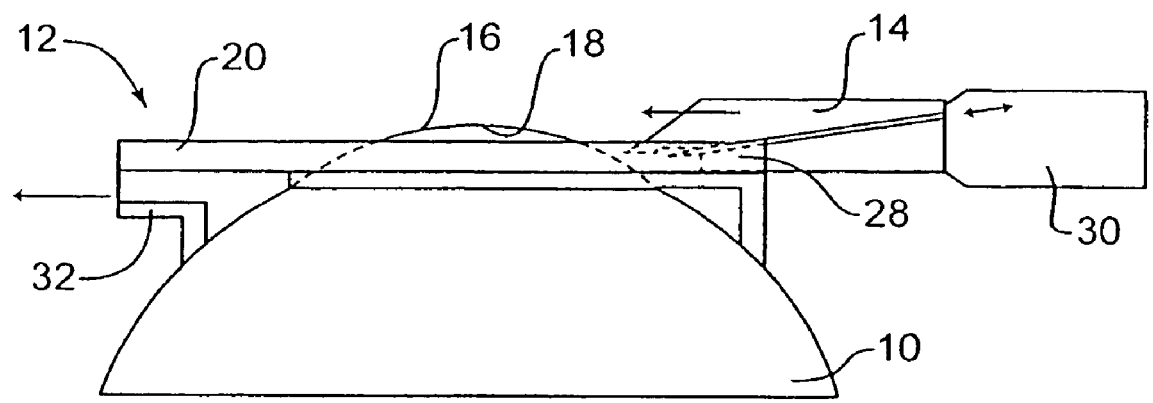
FIG. 1 is a diagram showing a side view of an eye and a cornea separator with a separator located in a first position according to the preferred embodiments.

FIG. 1 is a diagram showing a side view of an eye 10 of a patient and a cornea separator device 12. The cornea separator device 12 includes a separator 14, shown here in a first position located away from the eye 10. The separator 14 includes a device that can scrape the epithelium from the cornea such as a plate, a wire or a knife with a dull edge. The separator 14 removes an epithelium layer 16 located above a corneal surface 18 of the eye 10. The separator 14 is not sharp enough to excise corneal tissue during operation of the cornea separator device 12.

Figure 2:
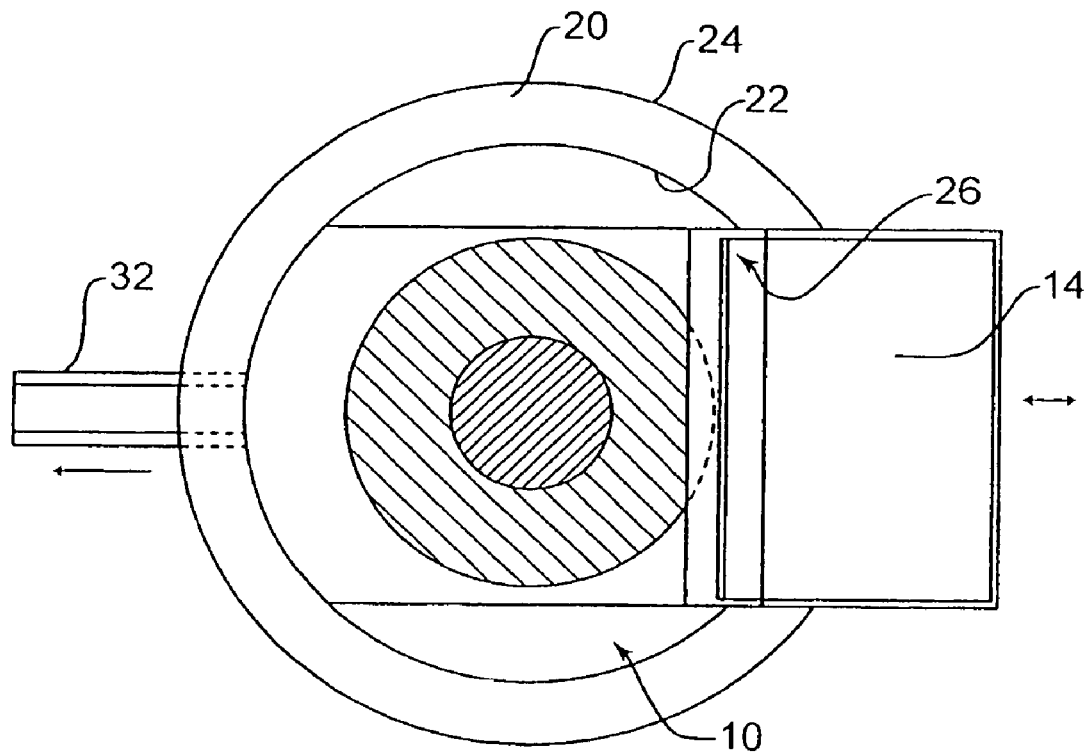
FIG. 2 is a diagram showing a top view of the eye and the separator located in a first position according to the preferred embodiments.

Referring also to FIG. 2, the cornea separator device 12 includes a ring 20 that sits on the eye 10 with its plane parallel to a limbus of the eye. The ring 20 includes an internal diameter 22 ranging from about 10 to about 12 mm and external diameter 24 from about 13 to about 16 mm and including a groove 26 (best seen in FIG. 15). The groove 26 is dimensioned wider than the internal diameter 22. A separator support 28 fits in the groove 26 to carry the separator 14 on a determined travel.

An oscillation device 30 provides motion and vibration to the separator 14. The oscillation device 30 can oscillate the separator 14 either transversely or longitudinally with frequency ranging from about 10 Hz to about 10 KHz. Electromagnetic or piezoelectric forces on the separator 14 can provide the oscillation, or external rotating or vibrating wires can provide the oscillation. To maintain the ring 20 on the eye 10, for example during oscillation, the ring 20 can include a circumferential groove 32 positioned on a side of the eye 10. Suction can be applied to the circumferential groove 32 to ensure stable mounting of the ring 20 to the eye 10.

Figure 3:
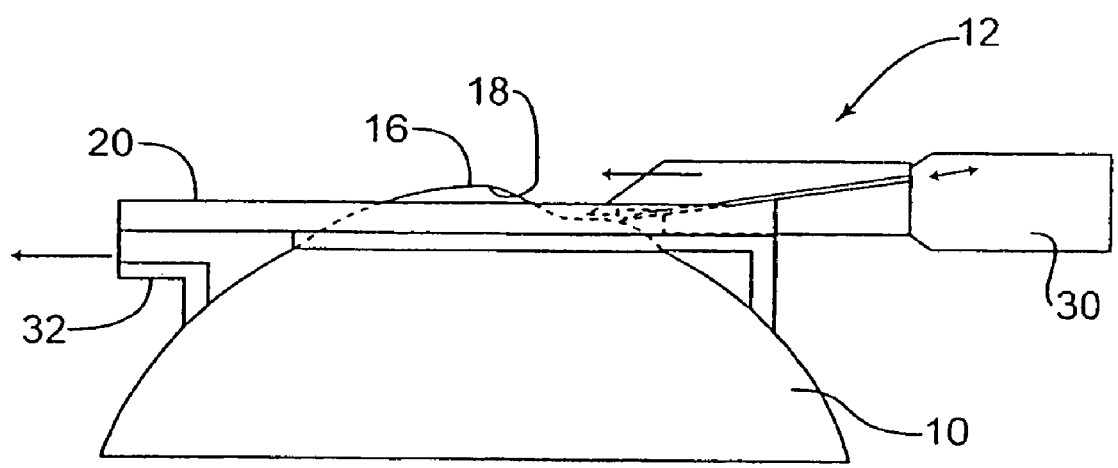
FIG. 3 is a diagram showing a side view of the eye and the separator located in a second position according to the preferred embodiments.
Figure 4:
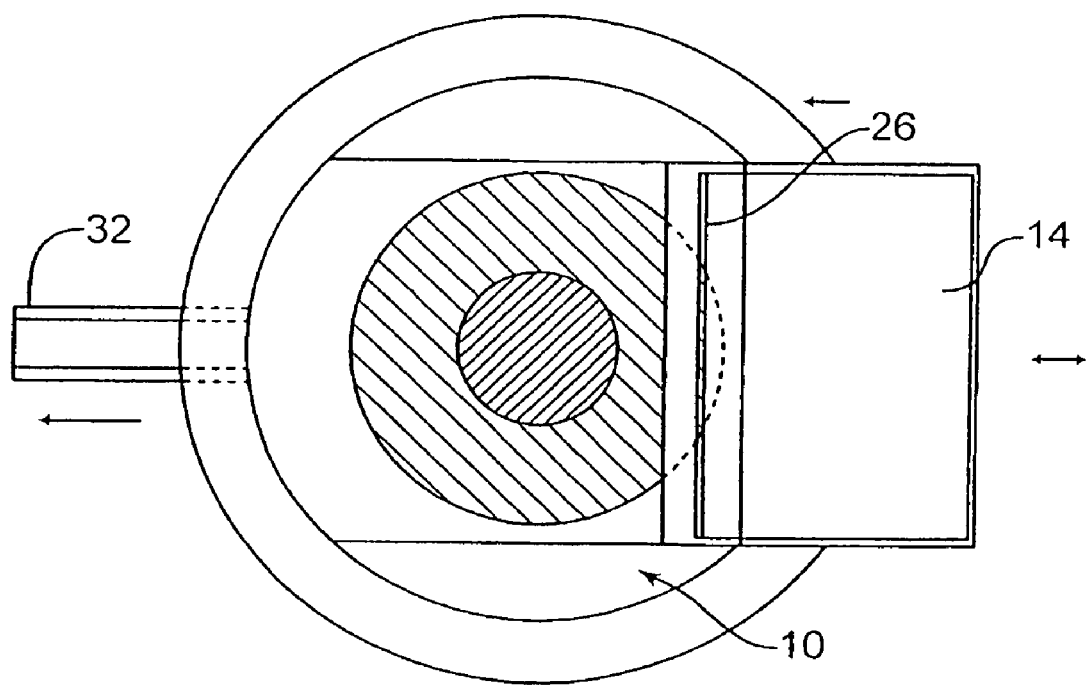
FIG. 4 is a diagram showing a top view of the eye and the separator located in a second position according to the preferred embodiments.

FIGS. 3 and 4 are diagrams showing a side and a top view, respectively, of the eye 10 and the separator 14 located in a second position with respect to the eye. As the separator 14 travels to contact the eye 10, the corneal surface 18 is flattened. To accommodate the travel of the separator 14, the separator support 28 freely slides in the groove 26, for example, when driven by the oscillation device 30.

Figure 5:
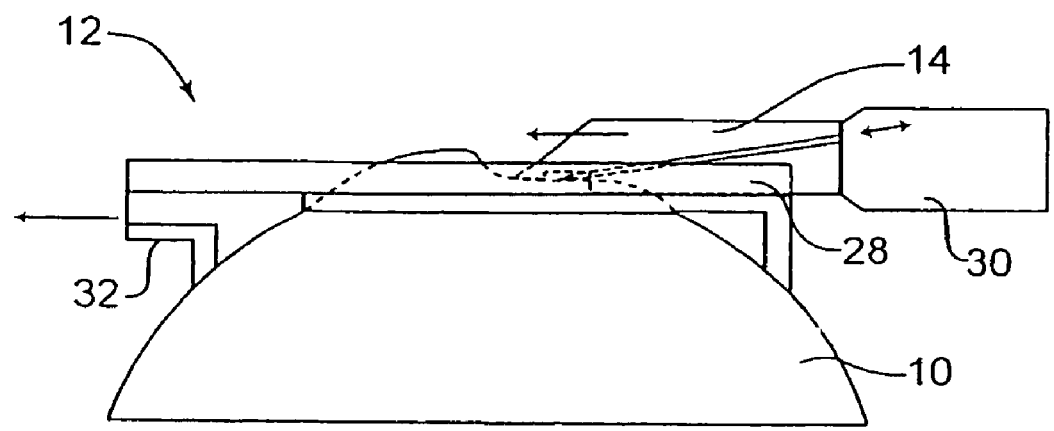
FIG. 5 is a diagram showing a side view of the eye and the separator located in a third position according to the preferred embodiments.
Figure 6:
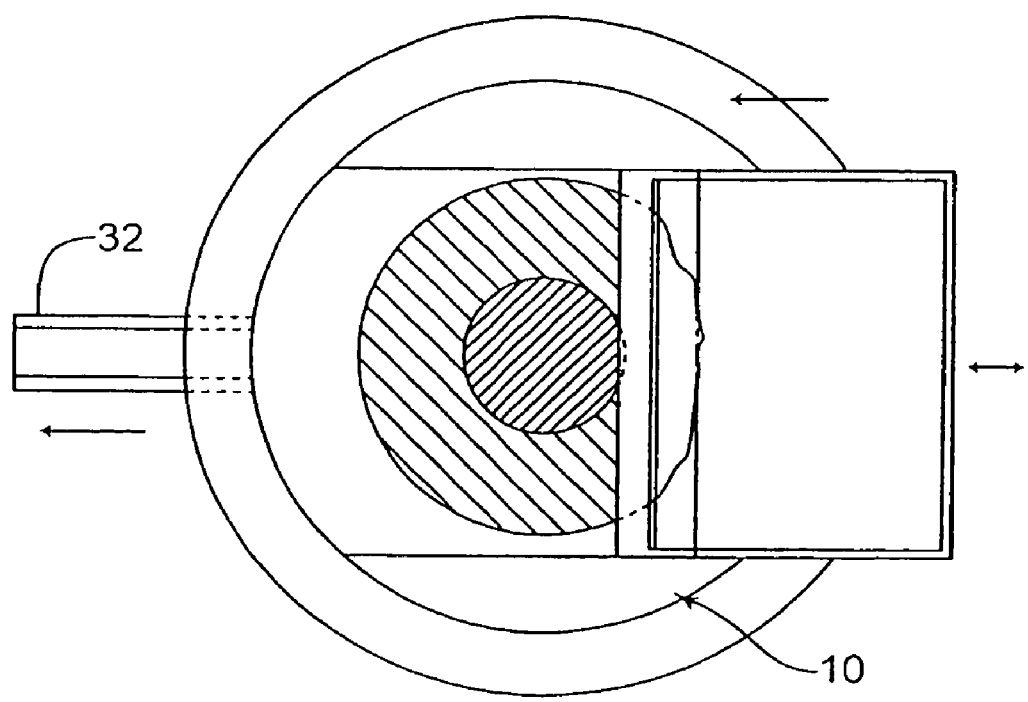
FIG. 6 is a diagram showing a top view of the eye and the separator located in a third position according to the preferred embodiments.

FIGS. 5 and 6 are diagrams showing a side and a top view of the eye 10 and the separator 14 located in a third position. As the separator 14 travels along the cornea 10, the epithelium layer 16 is separated from the cornea. The separator 14 separates the epithelium layer 16 without cutting the cornea 18.

Figure 7:
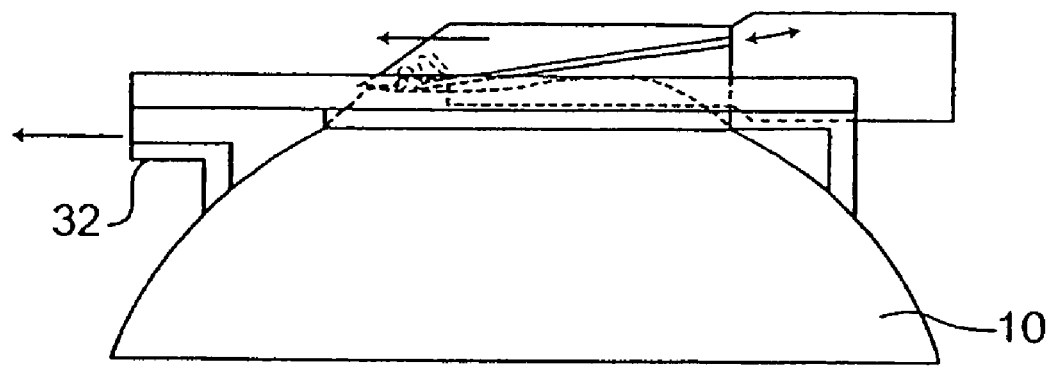
FIG. 7 is a diagram showing a side view of the eye and the separator located in a fourth position according to the preferred embodiments.
Figure 8:
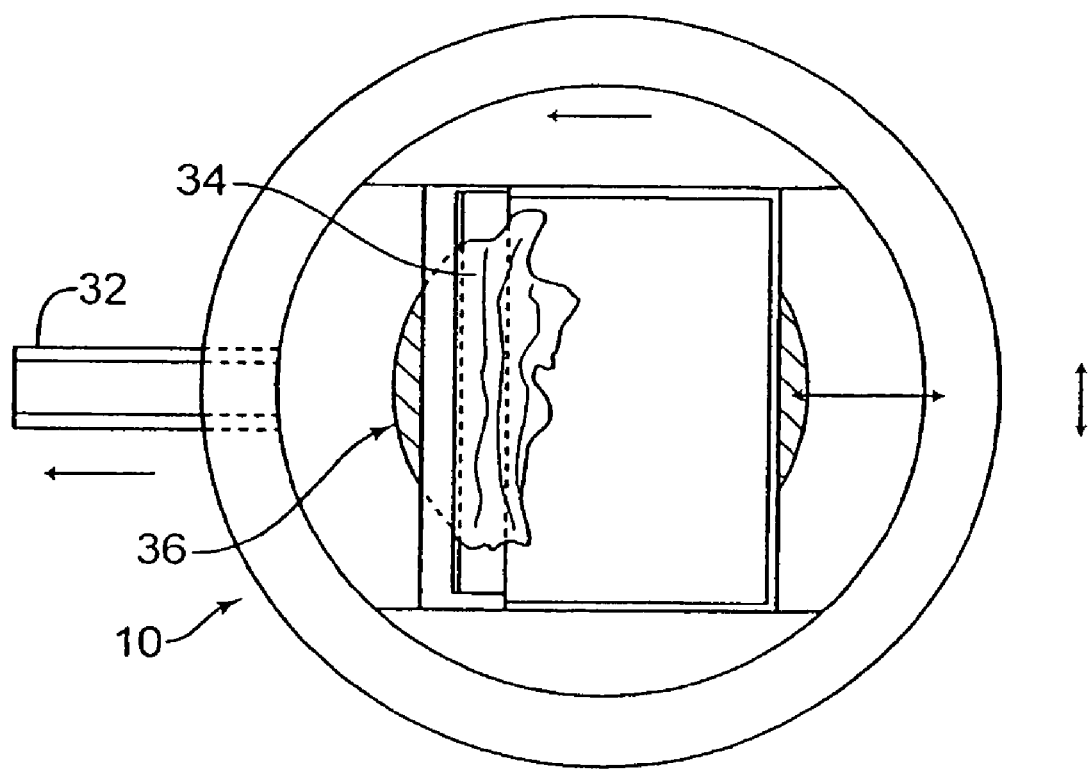
FIG. 8 is a diagram showing a top view of the eye and the separator located in a fourth position according to the preferred embodiments.

FIGS. 7 and 8 are diagrams showing a side and a top view of the eye 10 and the separator 14 located in a fourth position. In one embodiment, the travel of the separator 14 is controlled to produce an epithelial disk 34 hinged at an edge 36 of the epithelial disk 34. In another embodiment the epithelial disk 34 is completely detached for the corneal surface 18, for example, as described below.

Figure 9:
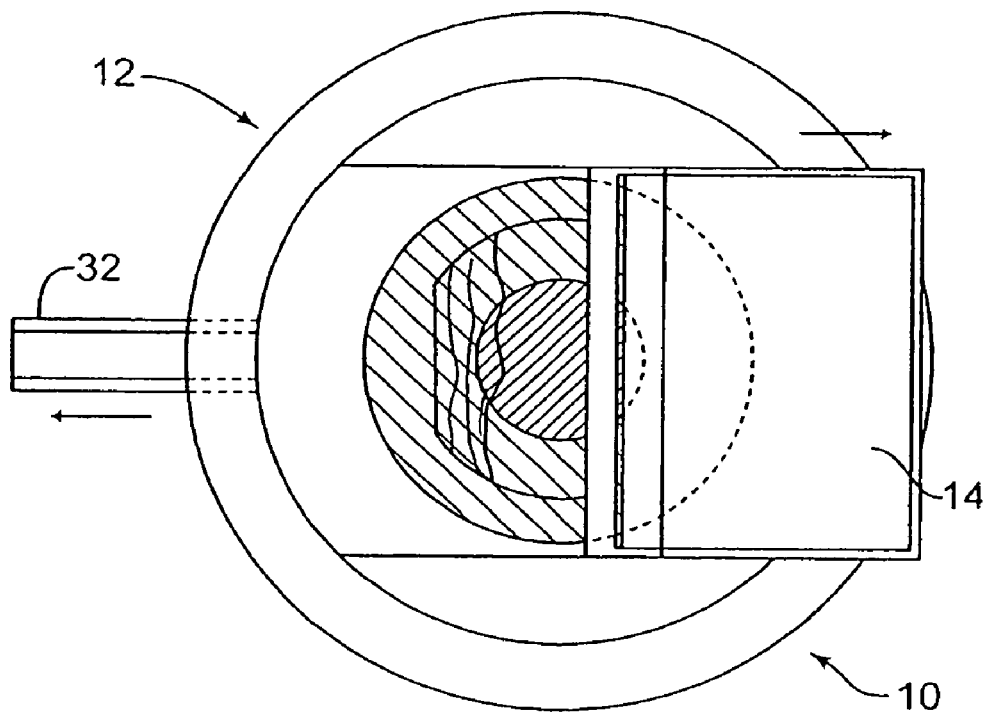
FIG. 9 is a diagram showing a top view of the eye and the separator located in a fifth position according to the preferred embodiments, the separator is retracted after epithelial separation.
Figure 10:
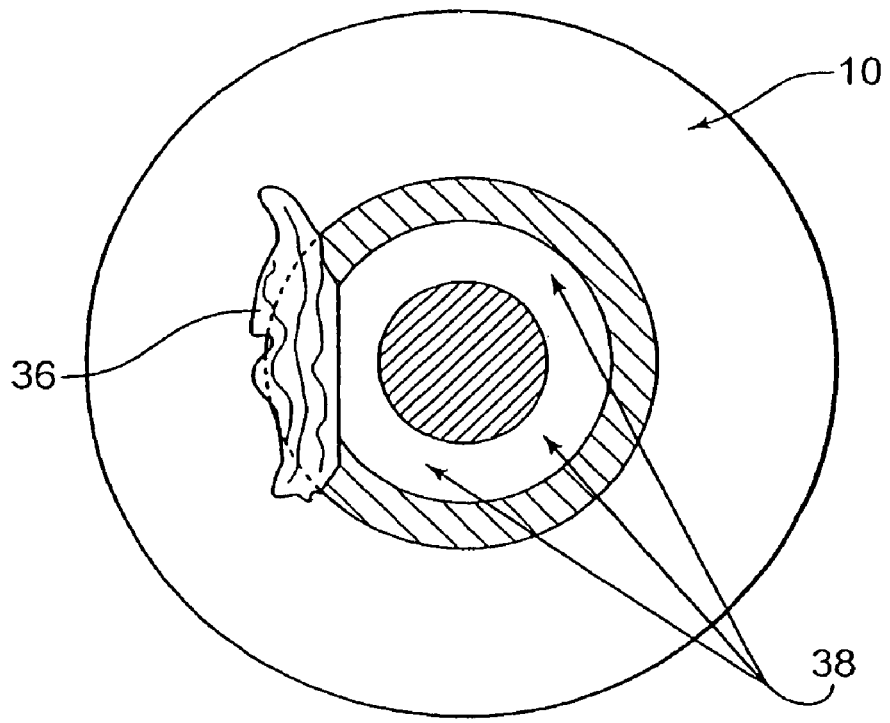
FIG. 10 is a diagram showing a top view of the eye with the separator removed.

FIG. 9 is a diagram showing a top view of the eye 10 and the separator 14 located in a retracted position after the epithelial disk 34 as been formed. After the separator 14 is retracted, suction to the circumferential groove 32 is turned off and the cornea separator device 12 is removed from the eye 10. Referring also to FIG. 10, after the cornea separator device 12 is removed, a deepithelialized area 38 is exposed that corresponds to a shape and size of the area that the separator 14 contacted during travel.

Figure 11:
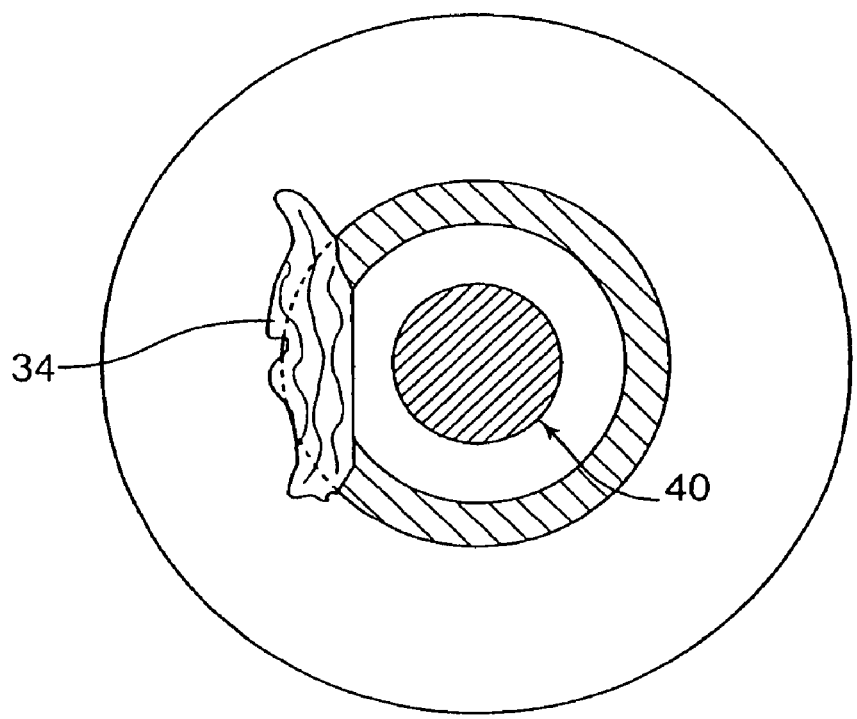
FIG. 11 is a diagram showing a top view of the eye after ablations is performed with a laser.
Figure 12:
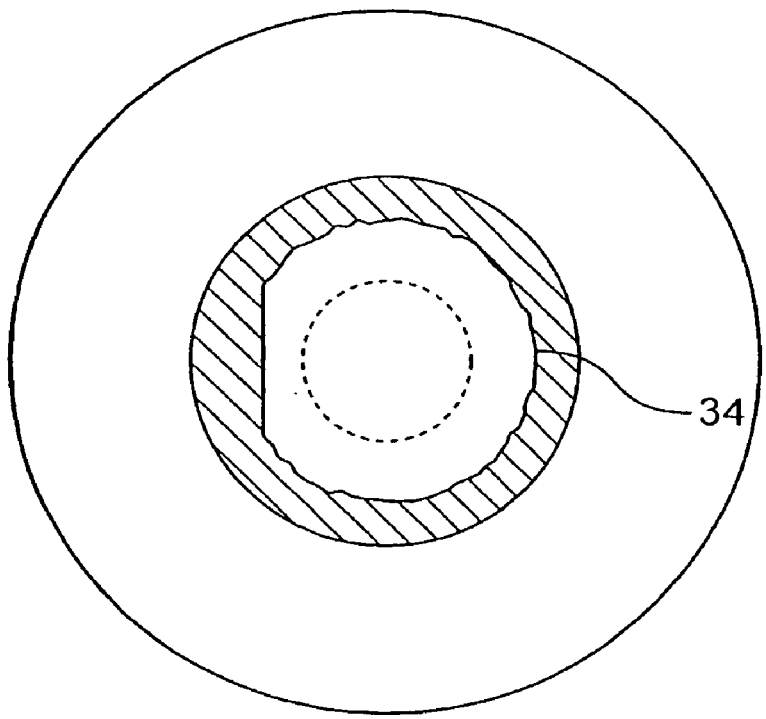
FIG. 12 is a diagram showing a top view of the eye with the epithelium replaced on the eye.
Figure 13:
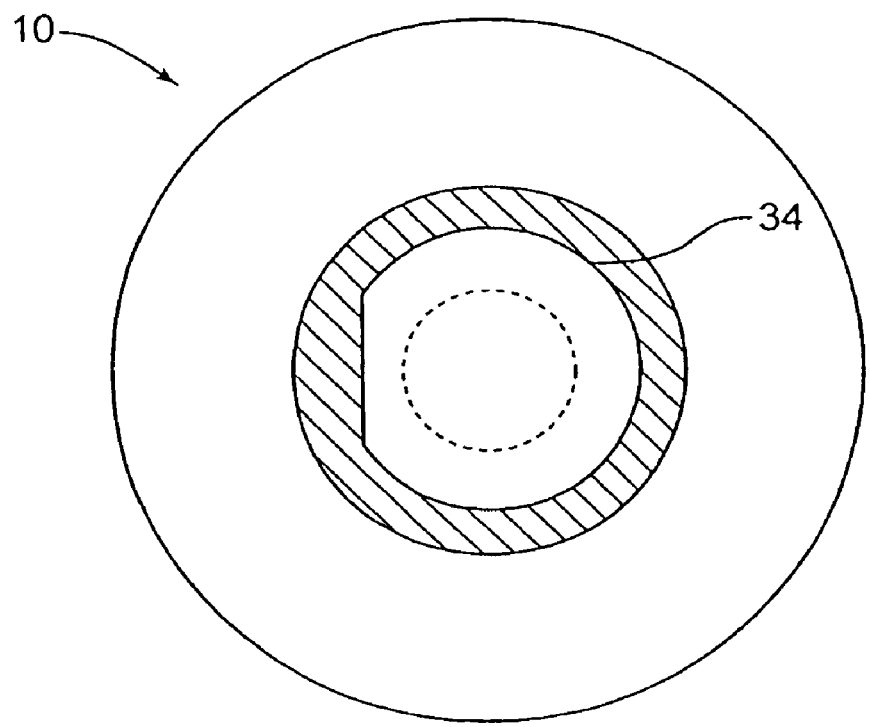
FIG. 13. is a diagram showing a top view of the eye with the epithelium smoothly stretched into place.

FIG. 11 shows a top view of the eye 10 after laser ablation is performed. The laser ablation forms an irradiated area 40 on the eye 10. Referring to FIG. 12, thereafter, the epithelium disk 34 is replaced on the corneal surface 18 of the eye 10 to aid in the healing process. Referring to FIG. 13, once replaced on the corneal surface 18, the epithelium disk 34 is preferably smoothly stretched into place.

Figure 14:
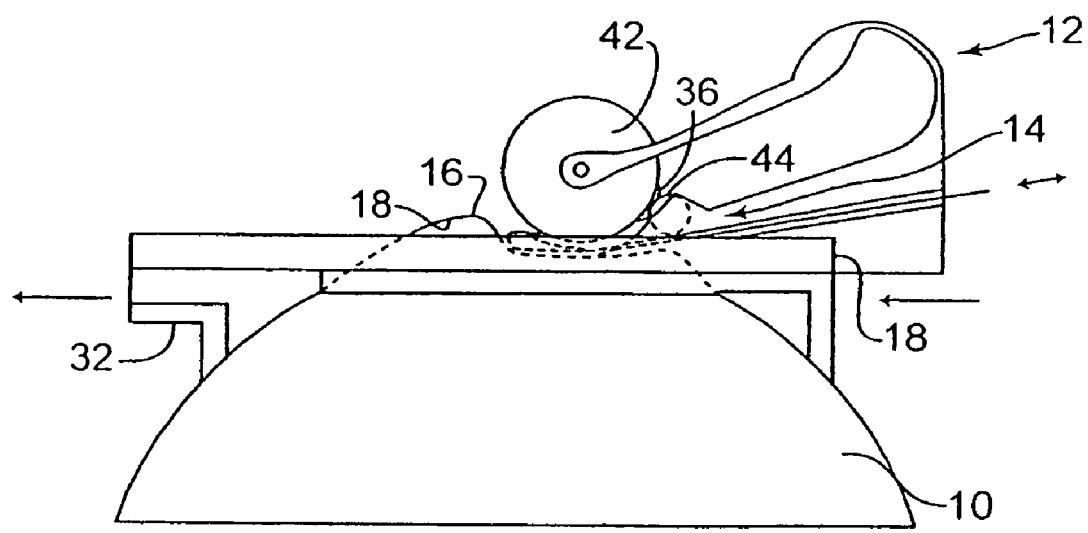
FIG. 14 is a diagram showing a side view of the eye and the cornea separator device including a rotating drum.
Figure 15:
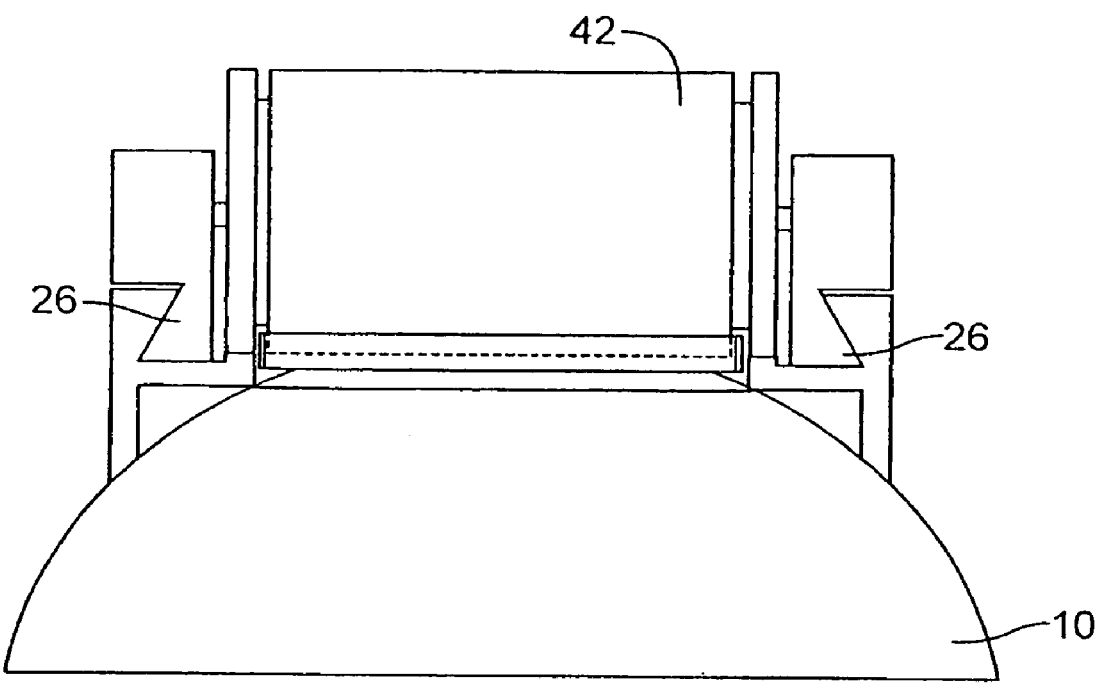
FIG. 15 is a diagram showing a front view of the eye and the cornea separator device including the rotating drum.
Figure 16:
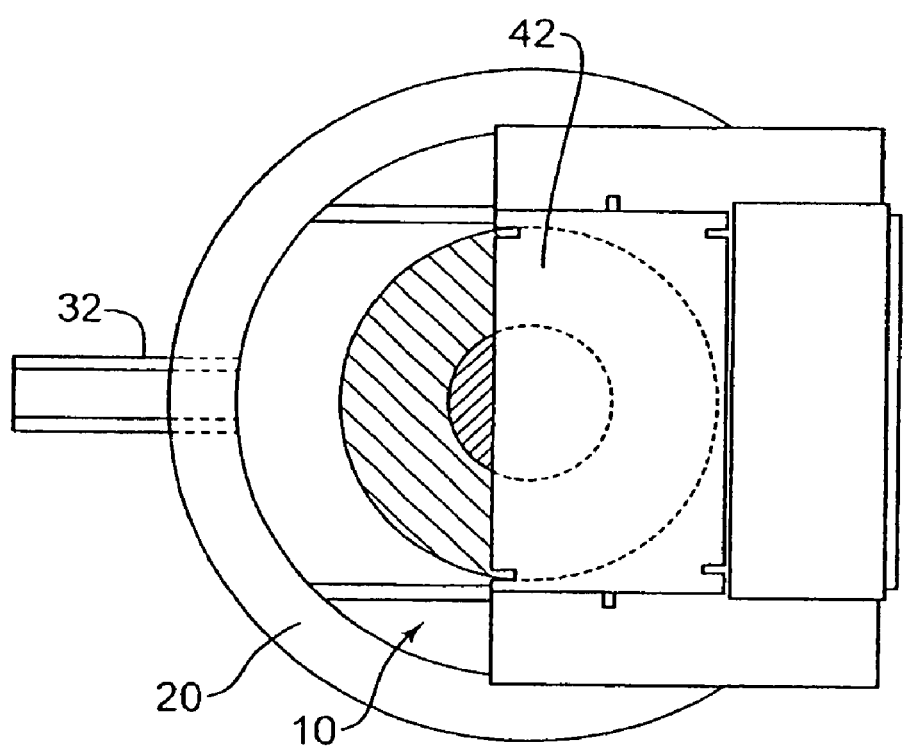
FIG. 16 is a diagram showing a top view of the eye and the cornea separator device including the rotating drum.

FIG. 14 is a diagram showing a side view of the eye 10 and the cornea separator device 12 including rotating drum 42. To rotate the drum 42, the cornea separator device 12 may include a rotating gear 44. The gear 44 could also be used to provide movement to the separator support 28. Referring also to FIGS. 15 and 16, front and top views, respectively, of the cornea separator device 12, the rotating gears 44 could be bilaterally placed on the separator support 28. The oscillating device 30 can provide for rotation of the gears 44 and the gears 44 can travel on rails, for example toothed rails, which run parallel to the groove 26.

Figure 17:
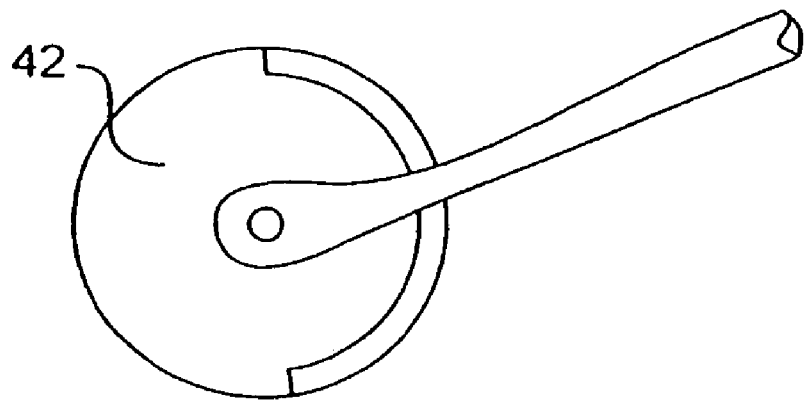
FIG. 17 is a diagram showing a drum according to one embodiment.

Since a typical thickness of an epithelial disk 36 includes about 50 microns, to preserve an epithelial disk 36, a separated epithelial disk 36 is rolled onto the drum 42. The drum 42 can include a diameter ranging from about 3 to about 9 mm and a length of about 12 mm. Referring also to FIG. 17, in one embodiment, to maintain integrity of the epithelial disk 36, the drum 42 can be coated with a hydrating and/or a conditioning substrate. The hydrating and/or conditioning substrate can include, for example, HEMA contact lenses, tissue culture media, silicone and biocompatible hydrogels. The hydrating and/or conditioning substrate can be removed from the drum after the epithelial disk 36 attaches on to the drum. Thereafter, the epithelial disk 36 can be removed from the drum 46 and replaced on the corneal surface 16, as described above.

Figure 18:
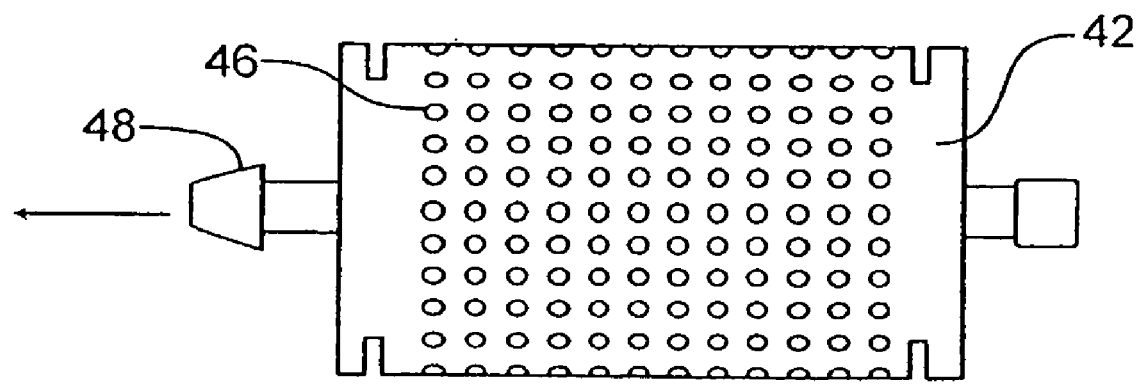
FIG. 18 is a diagram showing a drum according to another embodiment.

FIG. 18 shows another embodiment of the drum 42 includes apertures 46 and a connector 48 that connects to a suction source (not shown). By applying suction to the apertures 46 of the drum 42, the epithelial disk 36 can be rolled onto the drum 42. Thereafter, the epithelial disk 36 can be removed from the drum 46 and replaced on the corneal surface 16, as described above.

While the invention has been described above by reference to various embodiments, it will be understood that many changes and modifications can be made without departing from the scope of the invention. It is therefore intended that the foregoing detailed description be understood as an illustration of the presently preferred embodiments of the invention, and not as a definition of the invention. It is only the following claims, including all equivalents, which are intended to define the scope of this invention.

We claim:

1. An automated mechanical device to separate the epithelial layer of a cornea from the cornea, the device comprising:
   a separator, where said device can preserve the separated epithelial layer as a disk without rupturing said disk and without substantial epithelial cell loss;
   a ring configured to seat on the eye with its plane parallel to a limbus, and having an internal diameter ranging from about 10 to about 12 mm and external diameter from about 13 to about 16 mm including a groove, where said groove is wider than the internal diameter;
   a separator support that fits in said groove to carry the separator on a determined travel;
   an oscillation device that provides motion and vibration to the separator, wherein the separator oscillates with frequency ranging from about 10 Hz to about 10 KHz; and
   rotating gears where a motion of the separator support is provided by the rotating gears placed on the support, where rotation to the gears is provided by said oscillating device and said rotating gears are traveling on toothed rails that are parallel to the groove.

2. The device as claimed in claim 1 where said separator is not capable of excising corneal tissue during operation.

3. The device as claimed in claim 1 where a travel of the separator is controlled to produce an epithelial disk hinged to the border of separation.

4. The device as claimed in claim 1 where the ring includes a circumferential groove on the side of the eye and suction is applied to the circumferential groove to ensure stable mounting of the ring.

5. The device as claimed in claim 1 where the ring includes a circumferential groove on the side contacting the eye and suction is applied to ensure stable mounting of the ring.

6. The device as claimed in claim 1 where the separator oscillation is provided by electromagnetic forces on the separator.

7. The device as claimed in claim 1 where the separator oscillation is provided by piezoelectric forces on the separator.

8. The device as claimed in 1 where the separator oscillation is provided by external rotating or vibrating wires.

9. The device as claimed in claim 1 where the separator support freely slides in the groove.

10. The device as claimed in claim 9 where the separator support slides in the groove when driven by the oscillating device.

11. The device as claimed in claim 1 further including a rotating drum configured so that the separated epithelial disk is rolled on the drum.

12. The device as claimed in claim 11 wherein said drum includes a diameter ranging from about 3 to about 9 mm.

13. The device as claimed in claim 12 where said drum is coated with at least one of a hydrating substrate and a conditioning substrate.

14. The device as claimed in claim 13 where said at least one of the hydrating substrate and conditioning substrate is selected from the group consisting of HEMA contact lenses, tissue culture media, silicone and biocompatible hydrogels.

15. The device as claimed in claim 13 where said hydrating and conditioning substrate can be removed from the drum after the epithelial disk attaches on to the drum.

16. The device as claimed in claim 11 where said drum includes a hollow interior.

17. The device as claimed in claim 16 where a surface of the drum includes holes.

18. The device as claimed in claim 17 where said holes communicate with the hollow interior of the drum to connect to air suction through the hollow interior of said drum.

* * * * *